United States Patent
Cooper

(10) Patent No.: US 6,242,711 B1
(45) Date of Patent: Jun. 5, 2001

(54) ARC WELDING MONITORING SYSTEM

(75) Inventor: Edward L. Cooper, Clarklake, MI (US)

(73) Assignee: AccuData, Inc., Jackson, MI (US)

( * ) Notice: Subject to any disclaimer, the term of this patent is extended or adjusted under 35 U.S.C. 154(b) by 0 days.

(21) Appl. No.: 09/472,587

(22) Filed: Dec. 27, 1999

(51) Int. Cl.[7] ............................................. B23K 9/095
(52) U.S. Cl. ................................. 219/130.01; 219/147
(58) Field of Search ........................ 219/130.01, 147; 2/8

(56) References Cited

U.S. PATENT DOCUMENTS

| | | | |
|---|---|---|---|
| 2,045,800 | 6/1936 | Richter | 219/130.01 |
| 2,045,802 | 6/1936 | Richter | 2/8 |
| 2,351,910 | 6/1944 | Blankenbuehler | 219/130.01 |
| 4,555,614 | 11/1985 | Morris et al. | 219/130.01 |
| 4,677,277 | * 6/1987 | Cook et al. | |
| 4,716,273 | * 12/1987 | Paton et al. | |
| 4,721,947 | * 1/1988 | Brown | |
| 5,317,643 | * 5/1994 | Patricelli | |

* cited by examiner

Primary Examiner—Clifford C. Shaw
(74) Attorney, Agent, or Firm—Young & Basile, P.C.

(57) ABSTRACT

Apparatus for monitoring manual arc welding procedures for providing to the welder real-time monitoring of the welding characteristics to achieve optimum welds. The voltage and current conditions of the welding arc are instantly transferred within the visual range of the helmet wearing operator by the use of lights, illuminated bar graphs, light projections, illuminated see-through displays, or the like, located in proximity to the helmet viewing window wherein, through such monitoring, the operator is constantly aware of the arc conditions during welding.

3 Claims, 2 Drawing Sheets

ARC WELDING MONITORING SYSTEM

BACKGROUND OF THE INVENTION

1. Field of the Invention

The invention pertains to arc welding operations manually controlled by a welder. The voltage, current and other parameters of the arc during welding are monitored and visual indicating means located within the helmet worn by the operator visually provide the operator with information to produce high quality and repeatable welds.

2. Description of the Related Art

Semi-automated arc welding is achieved by the welder manually positioning the welding rod or welding wire producing the heat generating arc to the location being welded and such welding operations include stick welding, gas metal arc welding, submerged arc welding and tungsten inert gas welding. These manual welding operations necessarily rely upon the spacing of the electrode from the weld location to produce the desired arc to achieve optimum melting of the base and welding rod or wire metals, and the quality of the weld produced is directly controlled by the skill of the welder.

Skilled manual arc welders rely upon experience to achieve the desired arc, and the operator senses the arc characteristics by the welding sound, light produced and various conditions such as splash, sputtering and the like to determine the quality and effectiveness of the weld. However, even with skilled arc weld operators, it is difficult to manually consistently maintain optimum welding characteristics, and it is very difficult to maintain quality and reliability during manual arc welding procedures. Where high quality welds must be achieved in critical applications, inspections, x-rays, and expensive secondary operations are often necessary significantly adding to the cost of quality arc welding. The cost of identifying and re-working defective arc welds is seven to eight times the cost of the original weldment.

Efforts have been made to provide the manual arc welder with information during welding to improve the quality of the arc. In U.S. Pat. No. 4,677,277, the arc current and voltage is monitored to produce an audio indication to the operator as to the condition of the arc. However, monitors consisting only of audio arc parameter indicators are hard to hear and interpolate and are not capable of achieving the desired closeness of control and quality of weld often required.

OBJECTS OF THE INVENTION

An object of the invention is to reduce the variations which may occur in manual arc welding in order to improve the quality of the weld, obtain consistent repeatability for a single operator or between operators, and reduce variations in the manual arc welding process.

Another object of the invention is to provide arc welding monitoring apparatus wherein the manual arc welding process will become more stable, testable and certifiable as to render arc welding more competitive for critical joining applications wherein real-time monitoring of the weld is possible without solely relying strictly on operator certification and welding procedures may be validated at the weldment.

Yet another object of the invention is to provide arc welding monitoring apparatus wherein operators may be able to gauge their own performance and training time is reduced as real-time feedback is provided, and the arc welder's performance can be compared with a standard, other welders, or their own historical data.

A further object of the invention is to provide manual arc welding monitoring apparatus wherein real-time quality control is achieved and reduced requirements for safety factors will produce more economical yet higher quality welds than previously attainable, and weldment re-working is reduced and the overall cost of arc welding is lowered.

An additional object of the invention is to provide an arc weld monitoring apparatus wherein real-time defect identification is achieved whereby the operator can immediately respond to weld defects and post-process inspection and testing can be reduced with attendant cost savings.

SUMMARY OF THE INVENTION

In the practice of manual arc welding processes utilizing the apparatus of the invention, a welding torch or electrode holder for welding rods or welding wire is connected to a welding power supply capable of producing the desired current and voltage for achieving arc welding. The welding process is monitored by using sensors at the point of the weld to determine the rate of welding wire feed, for instance, and on the welding power supply equipment to sense the current and voltage. This sensor information is processed by a real-time electronic monitor which performs signal analysis from the sensor information and controls the visual indicating device located within the welder's helmet adjacent the helmet viewing window. The sensors are capable of sensing the arc voltage, current, wire speed, bead temperature and bead penetration, some of these parameters being estimatable upon knowing the arc voltage and current and wire speed.

A standard welding helmet having the usual darkened viewing window through which the welder observes the welding operation is provided with visual display elements controlled by the monitor receiving the information from the various sensors at the welding power supply and the arc. These visual sensors are preferably in the form of illuminated diodes, bulbs, bar graphs, video projectors or see-through displays such as may use liquid crystal indicia or the like.

Information received by the monitor with respect to the characteristics occurring during welding may be electronically recorded using an auxiliary personal computer or networked client computer wherein this information is available for post-process evaluation, historical comparison or quality analysis.

The visual indicating means within the helmet to inform the welder of the condition of the arc can take several forms. Preferably, the indicators are visual and are either located adjacent the helmet viewing window, preferably along the lateral sides of the window as to be within the peripheral vision range of the welder, or the visual indicating information may be projected directly upon the viewing window or superimposed thereover so as to be directly in the line of sight of the welder.

With the peripherally visual indicators located at the lateral sides of the viewing window, the indicators may take the form of light emitting diodes, or incandescent bulbs, or the indicator may take the form of an illuminated bar graph peripherally visible to the welder. When light emitting diodes are used, preferably, a plurality of lights may be employed on each side of the window wherein the lights are formed in sets and may be different colors to facilitate identification. For instance, the illumination of green LEDs can indicate that the welding characteristics are within desired parameters, and if the welding characteristics depart from acceptable characteristics, the red LEDs will illuminate. Of course, the LEDs may be a variety of colors and may be lit, or extinguished, according to any desired pattern.

When using a bar graph adjacent the element viewing window, the operator is able to immediately sense ideal conditions for arc welding as the bar graph will be "centered" under ideal welding parameters, and any departure from the ideal can be immediately determined by the operator and the necessary adjustments can be made to restore the desired welding characteristics.

It is also possible to locate a small video projector within the helmet for projecting desired data upon the inside surface of the viewing window wherein the operator can see through such data while observing the welding operation. As such data will be well within the view of the operator, the desired data can consist of lights, bar graphs, or any desired configuration of visual means for indicating the welding characteristics. Likewise, rather than using a video projector for the welding indicia, it is possible to have the indicia appear on a "see-through" liquid crystal display screen or the like superimposed over the helmet viewing window upon which the desired indicia appears.

It is also within the purview of the invention to include audio apparatus within the helmet, such as earphones, to emit audio vibrations which vary in accord with the welding characteristics, and such audio signals, while not as precise as the visual indicia provided in accord with the basic concept of the invention also augment the visual monitoring of the arc weld process and aid the welder.

BRIEF DESCRIPTION OF THE DRAWINGS

The aforementioned objects and advantages of the invention will be appreciated from the following description and accompanying drawings wherein.

DESCRIPTION OF THE PREFERRED EMBODIMENTS

Figure 1:
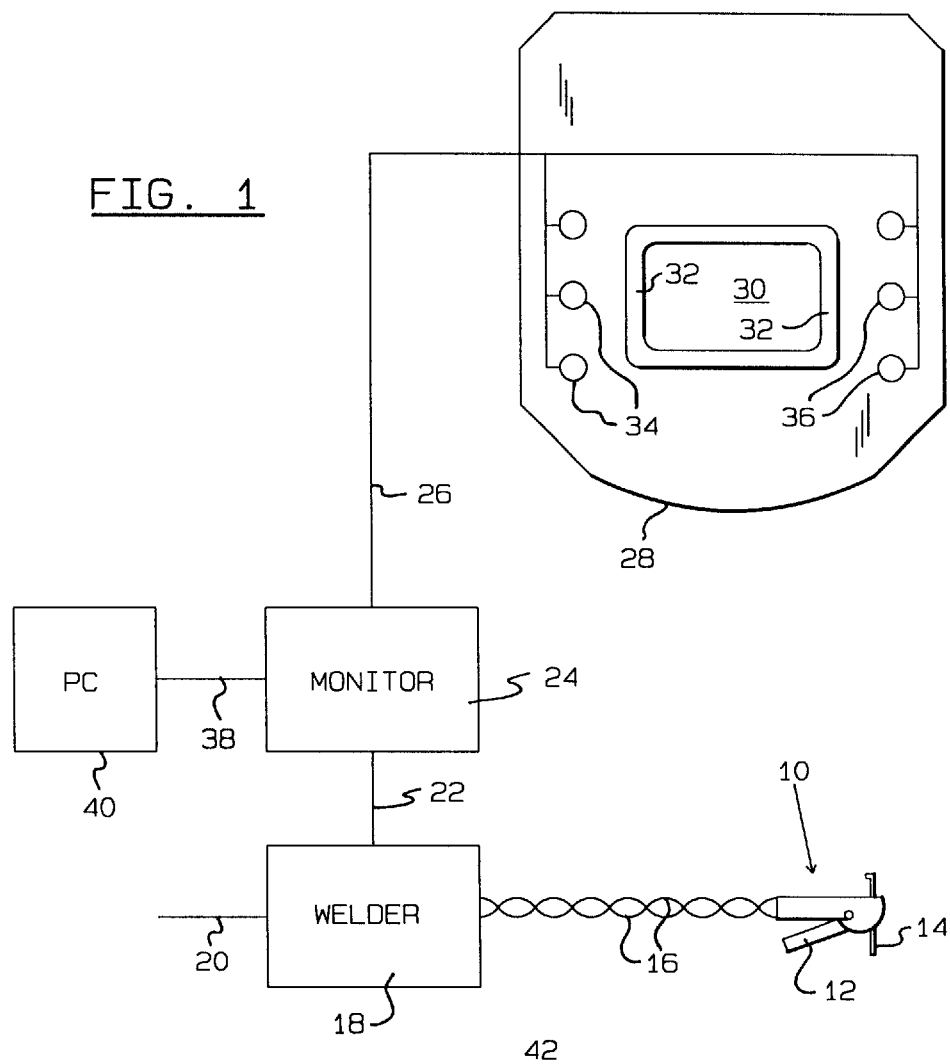
FIG. 1 is a schematic view of the arc welding monitoring system of the invention utilizing the embodiment of the visual indicating apparatus shown in FIG. 2.

A typical basic manual arc welding system utilizing the concepts of the invention is shown in FIG. 1 in a semi-schematic form. Such a manual arc welding system includes a hand held torch generally indicated at 10 which includes a spring biased clamp 12 for holding the electrode welding rod 14. It is to be understood that the electrode 14 may comprise welding wire fed from a dispenser, as is well known, and in such instance wherein a flux coated electrode is not used, inert gas flow occurs at the welding site to prevent oxidation. The inventive concepts can be used with either rigid welding rod electrodes or wire fed systems, both of which are well known in the art as are the conventional controls and sensors therefore.

The torch 10 is electrically connected by flexible conductors 16 to the welder power equipment 18 which produces the desired voltage and current necessary for arc welding, and the unit 18 may also control the gas flow and welding wire feed if the same are utilized. The welder equipment 18 is supplied with electricity through conductor 20 from a conventional power source, not shown.

Through conductor 22, the welder equipment 18 is connected to an adjustable electronic monitor 24. The monitor 24 has been previously set with respect to the desired welding characteristics and is capable of producing electronic signals through output conductor 26 indicative of the information received from the welder equipment 18 through the various sensors located within welder equipment 18 and torch 10, such as a voltage sensor, a current sensor, a gas flow sensor, a wire feed sensor and the like. This information is fed into the monitor 24 in real-time, and a comparison of such input signals to the desired conditions pre-adjusted in the monitor is made at very short intervals, for instance a tenth of a second apart.

The circuitry of the monitor 24 constitutes no part of the present invention as circuits are well known for receiving sensor signals, comparing such signals with pre-set standards and producing output signals for operating warning devices, see U.S. Pat. No. 4,677,277.

The operator will be wearing the usual arc welding protective helmet 28 which includes the darkened viewing window 30 having lateral side regions 32. As is well known, the helmet 28 may include head embracing members, not shown, and the helmet 28 will be mounted upon the welder's head whereby the welding operation can be viewed through window 30.

The monitor 24 produces output signals through conductor 26 determined by the pre-settings of the monitor, and these signals are supplied to indicating means located within the helmet 28. In the embodiment shown in FIGS. 1 and 2, the indicating means constitute two sets of light emitting diodes, or bulbs, 34 which are located adjacent the window lateral sides 32 within the peripheral vision range of the welder. Accordingly, even though the welder will be viewing the welding procedure through window 30, he will be conscious of the light produced by the diodes 34 and 36. For instance, the diodes 34 may be of a green color while the diodes 36 may be red. When the welding process is within the specified limits as pre-set into monitor 24, the green diodes 34 will be lit and the welder will be conscious of the fact that the welding procedure is proceeding properly. If the arc welding process passes outside of the process control limits pre-set in monitor 24, the red LEDs 36 will illuminate and the green LEDs 34 will be extinguished. This immediately indicates to the welder that the welding process is outside of the control limits and adjustments must be made at the electrode 14 to reestablish the desired welding characteristics.

By using a plurality of LEDs adjacent each window lateral side, each LED may represent a different character of the welding characteristics. For instance, one LED may represent voltage, another, current, and another, the rate of welding wire feed.

Because the diodes 34 and 36 produce an instantaneous indication to the welder as to the condition of the welding characteristics, errors occurring during welding are immediately sensed by the welder who may immediately make adjustments to restore the proper welding characteristics and the real-time visual indication to the welder of the welding characteristics permits high quality repeatable welds to be achieved on a consistent basis.

For quality control purposes, or to permit trainees to evaluate their performance, the signal producing output of the monitor 24 can be recorded through conductor 38 attached to a recording device such as a personal computer 40 wherein recording of the monitoring signals to the helmet 28 occurs during welding and is stored for later viewing and analysis.

Figure 3:
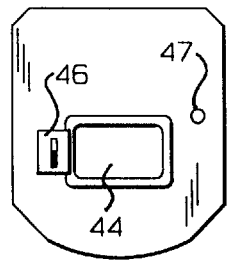
FIG. 3 is an elevational view of the inside of a welding helmet using a bar graph for providing visual indicating indicia.

It is possible to use the inventive concepts with various types of helmet mounted indicating devices, and in FIG. 3, another embodiment of welding characteristics indicating is illustrated. The helmet 42 includes the viewing window 44, and the welding characteristic indicating device constitutes a real-time electrically illuminated bar graph meter 46 for displaying qualitative welding information received from the monitor 24. The bar graph 46 can be set to indicate any particular element of the welding process and permits a qualitative means for obtaining an approximate value of any continuously changing variable desired. An LED 47 may be mounted within the helmet and is used in conjunction with the bar graph to indicate if a pre-determined element of the welding process is out of process control.

Figure 2:
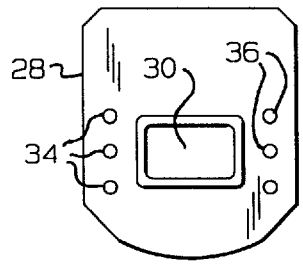
FIG. 2 is an elevational view of the interior of a welding helmet used in accord with the invention having light emitting diodes for producing the indicated indicia.
Figure 4:
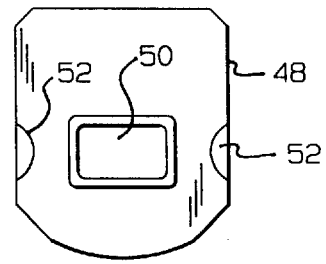
FIG. 4 is an elevational view of the inside of a welding helmet having audio indicating earphones located therein.

FIG. 4 illustrates a helmet 48 having a viewing window 50 wherein acoustic signals can be transmitted to the welder in addition to the visual means shown in FIGS. 1 and 2 or FIG. 3. In FIG. 4, the visual indicating means are not shown, but are present. The earphones 52 are located within the welding helmet, and may serve the welding operator in two distinct categories. During the welding process, tonal signals can be generated to indicate when the weld process has moved outside of established control limits and also, before and after welding occurs, the acoustical source may be used to relay verbal information to the operator about the welding process at hand. For instance, the computer 40 can be preset to identify the particular weld to be performed and notify the welder of any relevant setup information or warnings that are appropriate. After the welding operation has been completed, summary information about the weld can also be acoustically related to the welder.

Figure 5:
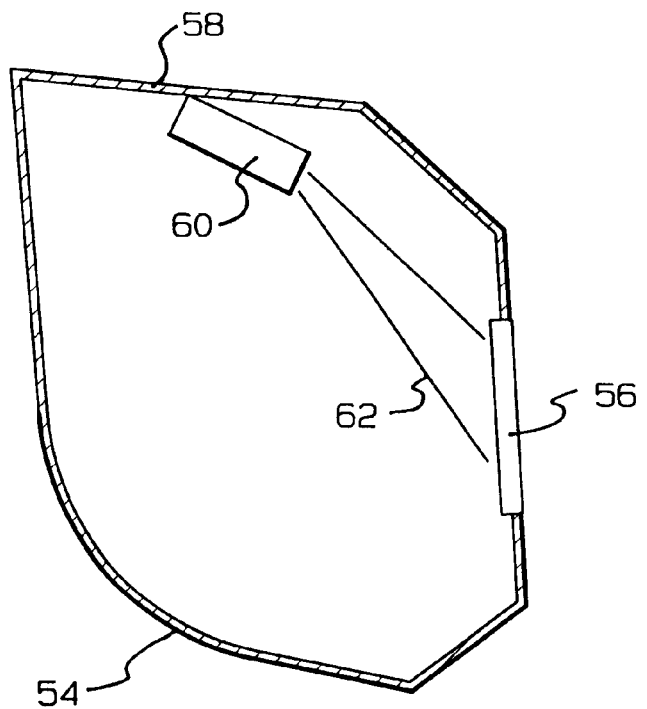
FIG. 5 is a side sectional schematic view of a welding helmet in accord with the invention illustrating a video projector for projecting welding indicia upon the helmet viewing window.

It is also within the inventive concepts to utilize visual welding characteristic indicating means other than those shown in FIGS. 1–3. In FIG. 5, a video projection arrangement is illustrated capable of conveying greater information to the operator than is possible with the LED and bar graph systems previously disclosed.

In FIG. 5, the welding helmet 54 includes the usual darkened viewing window 56 and the helmet includes the upper portion or panel 58. A video projection unit 60 is mounted to the inside of the panel 58, and the video projection unit may be hard wired, or connected by a wireless transmitter, to the monitor 24 or computer 40 wherein the video projection unit 60 produces a light beam 62 projected upon the inside surface of the viewing window 56. The particular data included in the light beam 62 is a real-time indication of the welding characteristics and the fact that this information is displayed on the inside surface of the viewing window 56 permits the information to be instantly viewable by the welder without interfering with the viewing of the welding process. As the interior of the helmet 54 is dark when worn by the operator, and as the inside surface of the window 56 is reflective and almost mirror-like in reflecting light from the inside of the helmet, the reflected information from the viewing window as contained in the beam 62 is easily visible and readable by the welder. With this system, it is possible for the welder to see information about the weld process before welding occurs, during the welding process, and after welding is completed. This "heads-up" display by video projection is capable of instantly transmitting to the welder's view a wide range of information with respect to the welding process.

Figure 6:
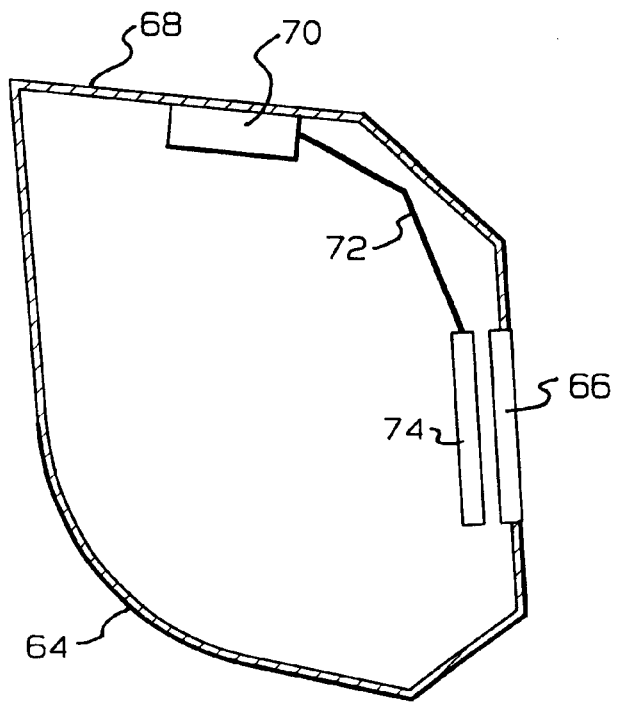
FIG. 6 is a side elevational sectional schematic view of an arc welding helmet employing a "see-through" display screen bearing welding indicia thereon superimposed over the helmet viewing window.

FIG. 6 illustrates another embodiment of means for providing a great deal of information to the welder. The embodiment shown in FIG. 6 constitutes a "heads-up" display utilizing a see-through display screen.

In FIG. 6, the helmet 64 includes the darkened viewing window 66 and the upper panel 68. A video display unit 70 is attached to the helmet upper panel 68 which in turn supports a bracket and conductor 72 supporting the see-through display screen 74 which is superimposed adjacent the helmet viewing window 66 between the welder and the viewing window. Accordingly, the information received by the video display unit 70 by hard wire or radio reception from monitor 24 appears upon the see-through screen 74 for viewing and interpretation by the welder. The display screen 74 may be of the known liquid crystal type and permits a wide variety of information that can be transferred to the view of the operator in real-time.

As the invention permits the welding characteristics to be instantly viewed by the operator during welding, a higher quality weld than previously attainable can be produced with excellent repeatability and control. The utilization of the invention reduces inspection costs and permits superior welds to be more economically produced than previously.

It is appreciated that various modifications to the inventive concepts may be apparent to those skilled in the art without departing from the spirit and scope of the invention.

What is claimed is:

1. An arc welder arc monitoring system for use with manual welder operator controlled systems having an arc welding helmet having an inner surface, an upper surface, and a viewing window having lateral sides, comprising, in combination, welder equipment producing an arc welding current and voltage, an electrode connected to said welder equipment producing an arc during welding, a monitor connected to said welder equipment sensing the electrical characteristics of the arc being produced during welding, visual indicating means within the helmet adjacent the viewing window connected to said monitor visually indicating the welding characteristics of the arc at said electrode to the welder operator, and electronic data storage means electrically connected to said monitor storing the welding characteristic signals received by said visual indicating means during welding.

2. In an arc welder arc monitoring system as in claim 1, said visual indicating means comprising a video projector located within the helmet projecting welding characteristic data upon the helmet viewing window.

3. In an arc welder arc monitoring system as in claim 1, said visual indicating means comprising an electronic transparent see-through display screen within the helmet superimposed over the helmet viewing window.

* * * * *

UNITED STATES PATENT AND TRADEMARK OFFICE
CERTIFICATE OF CORRECTION

PATENT NO. : 6,242,711 B1
DATED : June 5, 2001
INVENTOR(S) : Cooper

It is certified that error appears in the above-identified patent and that said Letters Patent is hereby corrected as shown below:

<u>Title page,</u>
Item [75], add the following Inventors:
-- Stephen P. Ivkovich, Horton, MI (US)
  John F. Zeiler, Horton, MI (US) --

Signed and Sealed this

Thirtieth Day of September, 2003

JAMES E. ROGAN
*Director of the United States Patent and Trademark Office*